United States Patent [19]

Pavone et al.

[11] Patent Number: 5,731,285
[45] Date of Patent: Mar. 24, 1998

[54] TACHIQUININE ANTAGONIST TRICYCLIC COMPOUNDS, PREPARATION OF SAME AND PHARMACEUTICAL COMPOSITIONS CONTAINING SUCH COMPOUNDS

[75] Inventors: Vincenzo Pavone, Naples; Angelina Lombardi, Guardia Sanframondi; Carlo Pedone, Naples; Carlo Alberto Maggi, Florence; Laura Quartara, San Sepolcro, all of Italy

[73] Assignees: A. Menarini Industrie Farmaceutiche; Laboratori Guidotti S.p.A.; Malesci-Istituto Farmacobiologico S.p.A., all of, Italy

[21] Appl. No.: 731,709

[22] Filed: Oct. 17, 1996

Related U.S. Application Data

[63] Continuation of Ser. No. 318,669, filed as PCT/EP93/00893, Apr. 13, 1993, abandoned.

[30] Foreign Application Priority Data

Apr. 15, 1992 [IT] Italy .................................. FI92A0089

[51] Int. Cl.$^6$ .................................................. A61K 37/00
[52] U.S. Cl. .................................................. 514/10
[58] Field of Search .......................... 514/9, 10, 11, 514/2; 530/318, 317, 320

[56] References Cited

FOREIGN PATENT DOCUMENTS

0412542  2/1991  European Pat. Off. .
2216529  10/1989  United Kingdom .

OTHER PUBLICATIONS

Ploux et al, PNAS, vol. 84, pp. 8095–8099, (Nov. 1987).
Dutta, CIPS, vol. 12. (8), pp. 781–789, (1987).
Zhang et al, Biopolymers, vol. 34, pp. 1165–1173, (1994).
McKnight et al, Br. J. Pharmacol., vol. 104, pp. 355–360, (1991).
Neuropeptides, "Structure-Activity Studies of Neurokinin A", vol. 13, pp. 263–270 (1989).
Br. J. Pharmacol., "Pharmacological Specificity of Novel, Synthetic, Cyclic Peptides as Antagonists at Tachykinin Receptors", vol. 104, pp. 355–360 (1991).
Biopolymers, "Backbone Cyclization: A New Method for Conferring Conformational Contraint on Peptides", vol. 31, pp. 745–750 (1991).
Peptides, Chem & Biol. Proc., "Cyclic ψ(CH$_2$NR)Peptide Neurokinin A Antagonists:Structure–Activity and Conformational Studies", 12th APA, p. 124 (1992).
Bioorganic Chemistry, "The Polyamide Method of Solid Phase Peptide and Oligonucleotide Synthesis", vol. 8, pp. 351–370, (1979).
Jacs, "Solid Phase Peptide Synethis. I. The Synthesis of a Tetrapeptide", vol. 85, pp. 2149–2154 (1963).
Int. J. Peptide Protein Res., "Applications of BPO Reagent in Solid Phase Synthesis", vol. 31, pp. 231–238 (1988).
Tetrahedron Letters, "Synthesis of Cyclic Peptides on Solid Support", vol. 32, No. 22, pp. 2639–2642 (1991).
J. Pharm. Sciences, "Synthesis of Cyclic Peptides", vol. 61, No. 9, pp. 1345–1356 (1972).
J. Org. Chem., "A New Synthetic Route to Tert–Butyloxy-carbonylaminoacyl-4-(oxymethyl)Phenylacetamidomethyl-Resin, An Improved Support for Solid–Phase Peptide Synthesis", vol. 43, No. 14, pp. 2845–2852 (1978).
Naunyn–Schmiedebergs Arch Pharmacol., "The Possible Existence of Multiple Receptors for Substance P", vol. 318, pp. 281–287 (1982).
Life Sciences, "Characterization of Neurokinin Receptors in Various Isolated Organs by the Use of Selective Agonists", vol. 41, pp. 2269–2278 (1987).
The Peptides, "Analysis, Synthesis, Biology", vol. 2, pp. 1–284 (1980).
Eur. J. Bioschem., "Nomenclature and Symbolism for Amino Acids and Peptides", vol. 138, pp. 9–37 (1984).

*Primary Examiner*—Ponnathapura Achutamurthy
*Assistant Examiner*—T. D. Wessendorf
*Attorney, Agent, or Firm*—Hedman, Gibson & Costigan, P.C.

[57] ABSTRACT

Tachyikinin antagonist compounds of the general formula:

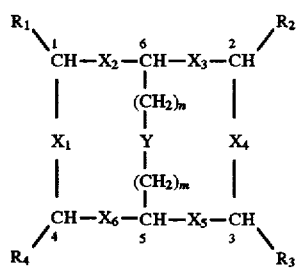

are described where: X1, X2, X3, X4, X5, and X6 are identical or different and are —NR'—CO— or —CO—NR"—, where R' is H or $C_{1-3}$ alkyl;

Y is —CONR—, —NRCO—, OCO, —COO—, —CH$_2$—NR—, —NR—CH$_2$—, —SS—, —CH$_2$—CH$_2$—, cis or trans —CH=CH— where R is H or $C_{1-3}$ alkyl;

R1, R2, R3, and R4 are each a hydrophobic group;

n and m are identical or different and are each a whole number from 1 to 4. The preparation and pharmaceutical compositions of the compounds are also disclosed.

21 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single (D) TOPOLOGY: circular (i i) MOLECULE TYPE: peptide (i x) FEATURE:
    (A) NAME/KEY: Modified-site
    (B) LOCATION: 5
    (D) OTHER INFORMATION: Xaa is Dpr (i x) FEATURE:
    (A) NAME/KEY: Modified-site
    (B) LOCATION: 1 and 6
    (D) OTHER INFORMATION: Met and Leu are bound together to form a first cyclo (i x) FEATURE:
    (A) NAME/KEY: Modified-site
    (B) LOCATION: 2 and 4
    (D) OTHER INFORMATION: Asp and Xaa are bound together to form a second cyclo (i x) SEQUENCE DESCRIPTION: SEQ ID NO: 1:

Met Asp Trp Phe Xaa Leu
1                    5

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: single
        (D) TOPOLOGY: circular (i i) MOLECULE TYPE: peptide (i x) FEATURE:
    (A) NAME/KEY: Modified-site
    (B) LOCATION: 5
    (D) OTHER INFORMATION: Xaa is Dpr (i x) FEATURE:
    (A) NAME/KEY: Modified-site
    (B) LOCATION: 1 and 6
    (D) OTHER INFORMATION: Met and Leu are bound together to give a monocyclo (x i) SEQUENCE DESCRIPTION: SEQ ID NO: 2:

Met Asp Trp Phe Xaa Leu
1                    5

TACHIQUININE ANTAGONIST TRICYCLIC COMPOUNDS, PREPARATION OF SAME AND PHARMACEUTICAL COMPOSITIONS CONTAINING SUCH COMPOUNDS

This is continuation of Ser. No. 08/318,669, filed Oct. 6, 1994, now abandoned, which was an application filed under 35 U.S.C. §371 based on PCT application EP93/00893, filed Apr. 13, 1993.

FIELD OF THE INVENTION

The present invention refers to compounds having general formula (I)

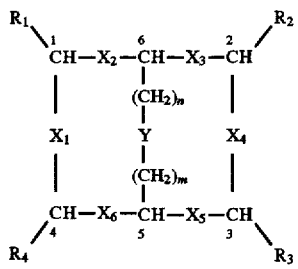

X1, X2, X3, X4, X5, and X6, identical or different, are each selected out of the group consisting of —NR'—CO—, —CO—NR'—, where R' is H or $C_{1-3}$alkyl Y is selected out of the group consisting of —CONR—, —NRCO—, —OCO—, —COO—, —$CH_2$—NR—, —NR—$CH_2$—, —SS—, —$CH_2$—$CH_2$—, cis or trans —CH=CH—, where R is H or $C_{1-3}$alkyl R1, R2, R3, and R4 are a hydrophobic group n and m, identical or different, are each a whole number from 1 to 4 the preparation of same and pharmaceutical compositions containing said compounds.

STATE OF THE ART

Tachykinin antagonist compounds are known from literature. Among them, particularly interesting are the cyclic compounds [GB-A-2 216 529; McKnight, British Journal of Pharmacology, 104, 2 (1991); Gilon et al., Biopolymers, Vol. 31, 745–750 (1991); Harbeson et al., Peptides, Chemistry and Biology Proceedings 12th APS, 124 (1992), Ed. Escom].

Although the chemical formula of the compounds considered herein is considerably different from that of the compounds already known, the pharmacological activity of the former is equal to or even higher than that of the latter. Therefore, the claimed compounds may be regarded as valid alternatives.

DETAILED DESCRIPTION OF THE INVENTION

The present invention refers to new products of general formula (I)

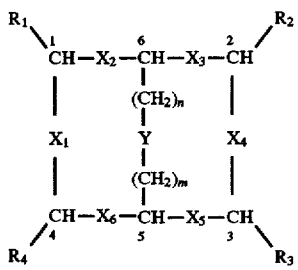

where:

X1, X2, X3, X4, X5, and X6, identical or different, are each selected out of the group consisting of —NR'—CO—, —CO—NR'—, where R' is H or $C_{1-3}$alkyl Y is selected out of the group consisting of —CONR—, —NRCO—, —OCO—, —COO—, —$CH_2$—NR—, —NR—$CH_2$—, —SS—, —$CH_2$—$CH_2$—, cis or trans —CH=CH—, where R is H or $C_{1-3}$alkyl R1, R2, R3, and R4 are each a hydrophobic group n and m, identical or different, are each a whole number from 1 to 4 the processes for the preparation of same and pharmaceutical compositions containing such compounds.

As may be seen, the compounds as per formula (I) described above exhibit several chiral centres: it is understood that also the various enantiomers are an object of the present invention.

Hydrophobic groups R1, R2, R3, and R4 preferably consist of the side chains of hydrophobic amino acids, both natural and synthetic, or of the side chains of non-hydrophobic amino acids whose functional groups were derivatized in order to render them hydrophobic.

In particular, R1, R2, R3, and R4 may be selected out of the following groups:

a) linear or branched alkyl groups of the type $C_nH_{2n+1}$ where n=0, 1 to 4 b) linear or branched alkyl groups of the type $C_nH_{2n}$—U—W where n=1 to 4; U=O, CO, COO, CONH, S, guanidine, NH and W=H, hydrophobic group containing 1 to 10 carbon atoms c) $CH_2C_6H_3XY$ where X and Y, identical or different, are each H, halogen, OH, $NH_2$, $CH_3$ in an ortho or meta or para position of the benzene ring d) $CH_2C_6H_4X$ where X=OR, SR, NHR, where R=hydrophobic group containing 1 to 10 carbon atoms e) $C_6H_3XY$ where X and Y, identical or different, are each H, halogen, OH, $NH_2$, $CH_3$ in the ortho or meta or para position of the benzene ring f) $CH_2C_6H_{11}$ g) 1-methyl-naphthyl, 2-methyl-naphthyl h) $CH_2$—imidazole i) $CH_2$—indole l) $CH_2$—(furanyl-3-yl)

m) $CH_2$—(pyridyl-3-yl)

n) $CH_2$—(imidazolyl-3-yl)

o) an eventually substituted, —$(CH_2)_3$— group, which cyclizes with one of the two adjacent groups X to give the side chain of proline, hydroxyproline, dehydroproline.

In particular substituents R1, R2, R3, and R4 may be the side chains of hydrophobic natural amino acids selected out of the group consisting of: glycine, alanine, valine, leucine, isoleucine, methionine, phenylalanine, tyrosine, tryptophan, proline, histidine. R1, R2, R3, and R4 may also be the hydrophobic-derivatized side chains of non-hydrophobic amino acids selected out of the group consisting of: serine, threonine, cysteine, aspartic acid, asparagine, glutamic acid, glutamine, t-carboxyglutamic acid, arginine, ornithine, lysine.

R1, R2, R3, and R4 may also be the side chains of hydrophobic not natural amino acids selected out of the group consisting of: norleucine, norvaline, alloisoleucine, dehydroproline, hydroxyproline, cyclohexylglycine (Chg), α-amino-n-butyric acid (Aba), cyclohexylalanine (Cha), aminophenylbutyric acid (Pba), phenylalanines mono- and disubstituted in the ortho, meta, or pars position of the aromatic ring with one or more of the following groups: $C_{1-10}$alkyl, $C_{1-10}$alkoxyl, halogen, β-2-thienylalanine, β-3-thienylalanine, β-2-furanylalanine, β-3-furanylalanine, β-2-pyridylalanine, β-3-pyridylalanine, β-4-pyridylalanine, β-(1-naphthyl)alanine, β-(2-naphthyl)alanine, 0-alkylated derivatives of serine, threonine, tyrosine, S-alkylated cysteine, S-alkylated homocysteine, alkylated lysine, alkylated ornithine, 2,3-diaminopropionic acid.

Out of the products as per formula (I) as defined above, particularly preferred are the products in which:

1) R1=—CH$_2$CH(CH3)$_2$
R2=—CH$_2$C$_6$H$_5$

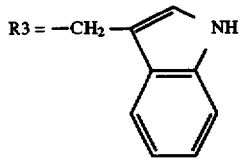

R4=—(CH$_2$)2—SCH$_3$
X1=X2=X3=X4=X5=X6=—CONH—
Y=—CONH—
wherein chiral carbon atoms exhibit L-configuration 2) Y=—NHCO—
the other substituents being as defined under point (1)

3) R4=—CH$_2$—C$_6$H$_{11}$
the other substituents being as defined under point (1)

4) Y=—NHCO—
the other substituents being as defined under point (3)

5) R2=R4=—CH$_2$—C$_6$H$_5$

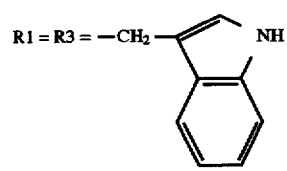

the other substituents being as defined under point (1)

6) Y=—NHCO—
the other substituents being as defined under point (5)

7) Y=—SS—
the other substituents being as defined under point (1)

8) Y=—CH$_2$—CH$_2$—
the other substituents being as defined under point (1)

9) Y=—CH=CH— (cis)
the other substituents being as defined under point (1)

10) Y=—CH=CH— (trans)

the other substituents being as defined under point (1)

11) m=n=1
the other substituents being as defined under point (1)

12) m=1, n=2
the other substituents being as defined under point (1)

13) m=1, n=3
the other substituents being as defined under point (1)

14) m=1, n=4
the other substituents being as defined under point (1)

15) m=2, n=1
the other substituents being as defined under point (1)

16) m=2, n=2
the other substituents being as defined under point (1)

17) m=2, n=3
the other substituents being as defined under point (1)

18) m=2, n=4
the other substituents being as defined under point (1)

19) X1=X2=X3=X4=X5=X6=—NHCO—
the other substituents being as defined under point (1)

20) Y=—NHCO—
the other substituents being as defined under point (19)

21) R4=—CH$_2$—C$_6$H$_{11}$
the other substituents being as defined under point (19)

22) Y=—NHCO—
the other substituents being as defined under point (15)

23) R2=R4=—CH$_2$—C$_6$H$_5$

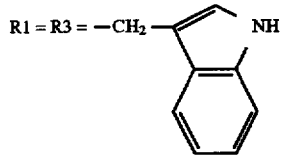

the other substituents being as defined under point (19)

24) Y=—NHCO—
the other substituents being as defined under point (23)

25) Y=—SS—
the other substituents being as defined under point (19)

26) Y=—CH$_2$—CH$_2$—
the other substituents being as defined under point (19)

27) Y=—CH=CH— (cis)
the other substituents being as defined under point (19)

28) Y=—CH=CH— (trans)
the other substituents being as defined under point (19)

29) m=n=1
the other substituents being as defined under point (19)

30) m=2; n=4
the other substituents being as defined under point (19)

31) the carbon atoms in positions 5 and 6 exhibit D-configuration
all substituents being as defined under point (1)

32) all chiral carbon atoms exhibit D-configuration
all substituents being as defined under point (1)

The compounds as per formula (I) covered by the invention can be prepared by known synthesis techniques, cf e.g. Schroeder et al., "The Peptides", Vol. 1, Academic Press, 1965; Bodansky et al., "Peptide Synthesis", Interscience Publishers, 1966; Barany and Merrifield, "The Peptides: Analysis, Synthesis, Biology", 2, Ch. 1, Academic Press, 1980.

The methods selected for the obtainment of the aforesaid products are the following:

i) synthesis in solution of the linear peptide chain by the coupling of suitably activated N-protected amino acids with an amino acid or a C-protected peptide chain, with intermediates isolation, followed by selective deprotection of C- and N-terminal chains, cyclization in organic polar solvents dilute solution. selective deprotection of the side chains and their cyclization in organic polar solvents dilute solution (cf also Bodansky-Bodansky, "The procedure of peptide synthesis", Springer Verlag, 1984).

ii) peptide chain solid phase synthesis from C-terminal end to N-terminal end on an insoluble polymer support, cyclization in the solid phase of previously deprotected side chains, followed by detachment from the polymer support by hydrolysis in anhydrous hydrofluoric acid containing suitable scavengers or in trifluoracetic acid containing suitable scavengers and cyclization of monocyclic peptide in organic polar solvents dilute solution. The process described above can alternatively consist of peptide chain solid phase synthesis from C-terminal end to N-terminal end on an insoluble polymer support, detachment from the polymer support by hydrolysis in anhydrous hydrofluoric acid containing suitable scavengers or in trifluoracetic acid containing suitable scavengers, cyclization of C-terminal and N-terminal ends in organic polar solvents dilute solution, deprotection of side chains and their cyclization in organic polar solvents dilute solution (cf the method described by Atherton et al. in Bioorganic Chemistry, 8, 351, 1979; by Merrifield in J. Am. Chem. Soc., 85, 2149–2154 (1963)). The first cyclization reaction can be carried out directly on the insoluble solid support (cf A. M. Felix et al., Int. J. Pep. Prot. Res., 31, 231, 1988; P. Rovero et al., Tetrahedron Letters, 32, 23, 2639 (1991), whereas the second cyclization can be carried out also in solution according to the procedures well known in the chemistry of peptide linkages (of Kopple K. D., J. Pharmaceutical Sci., 61, 1345, 1972). According to a particular method, the desired product may be obtained with PAM-resin (phenylacetoamidomethyl resin—A. R. Mitchell et al., J. Org. Chem., 43, 2845, 1978) functionalized with a Boc group protected amino acid at the N-terminal end. The amino acids directly bound to the resin are preferably the hydrophobic ones, such as Leu. After introduction of the other amino acids in the sequence, a first cyclization may be carried out reaching the side chains of the preferred aminoacids after their selective deprotection and activation. The monocyclic peptide can be removed by liquid hydrofluoric acid. The free peptide at N- and C-terminal ends can be further cyclized according to traditional synthesis methods.

The compounds as per formula (I) defined above proved to be more effective tachykinin antagonists than other analogous antagonists; it follows that—compared with the known products—they may be administered at lower dose levels.

Therefore, they are suitable for the treatment of arthritis, asthma, inflammations, tumoral growth, gastrointestinal hypermotility, Huntington's disease, neuritis, neuralgia, migraine, hypertension, incontinence of urine, urticaria, carcinoid syndrome symptoms, influenza and cold.

The compounds as per formula (I) covered by the invention are suitable for therapeutic administration to animals and man by the parenteral, oral, inhalatory, and sublingual ways, with pharmacological effects matching the described properties. In case of parenteral administration (intravenous, intramuscular, intradermal), the compounds to be used are sterile solutions or freeze-dried preparations. In case of oral administration, preparations such as tablets, capsules and syrups are conveniently used. Suitable dosed ointments and creams are utilizable by the dermic way. In case of nasal instillation, inhalation, and sublingual administration, the compounds to be used are respectively aqueous solutions, aerosol preparations, or capsules.

Active ingredient doses in the aforesaid compositions range from 0.1 to 10 mg/kg body weight.

EXAMPLE 1

Preparation of cyclo(Met—Asp—Trp—Dpr—Phe—Leu) SEQ ID NO: 1
 1                              5

[Compound as per formula (I) where: $Y=X1=X2=X3=X4=X5=X6=$—CONH—; $m=n=1$; $R1=$—$CH_2$—$CH(CH_3)_2$;

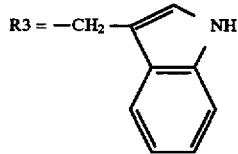

; $R2=$—$CH_2$—$C_6H_5$; $R4=$—$CH_2$—$CH_2$—$SCH_3$; and carbon atoms $C_1$, $C_2$, $C_3$, $C_4$, $C_5$, $C_6$ have L-configuration]

Compound (1)

a) Synthesis of the monocyclic peptide having the following sequence: H-Met-Asp-Trp-Phe-Dpr-Leu-OH SEQ ID NO:2

0.625 Grams Boc-Leu-OCH$_2$—PAM resin (Applied BioSystem, USA, 0.8 meq/g), equal to 0.5 mmoles of amine groups, is fed an Applied BioSystem 430A (Foster City, Calif., USA) semi-automatic peptide synthesis reactor. The Boc group is hydrolyzed with 33% TFA in DCM for 1.5 min. and with 50% TFA in DCM for 18.5 min.; then it is neutralized with in DMF with 10% DIEA solution fop 2 min. The following residues are made to react in the same order, in the quantities indicated in brackets: Boc-Dpr(Fmoc)-OH (0.852 g), Boc-Phe-OH (0.512 g), Boc-Trp(CHO)-OH (0.664 g), Boc-Asp(OFm)-OH (0.822 g).

The first acylation lasts 1 hour. The resin is washed and the reaction is ninhydrin-tested by the Kaiser method. In case of a negative response, the Boc group is hydrolyzed as described above, before the subsequent amino acid coupling. Acylation with Boc-Dpr(Fmoc)-OH is performed by adding an 5mino acid (2 mmoles) and PFBop (2 mmoles) solution in DMF to the deprotected resin. Boc-Phe-OH and Boc-Trp (CHO)-OH are coupled in the form of symmetric anhydride by dissolving 2 mmoles amino acid in 5 ml dichloromethane. The solution temperature is brought to 0° C. and 1 ml of a 0.5M solution of dicyclohexyl carbodiimide in dichloromethane is added. After 15 minutes, dicyclohexylurea is filtered and the resulting solution is added to the deprotected resin. Boc-Asp(OFm)-OH coupling is performed by adding the deprotected resin with an amino acid (2 mmoles) and HOBt (2 mmoles) solution in DMF; after 2 minutes, the suspension is added with a 0.5M solution of DCC in DCM (4 ml). The fluorenyl groups on Asp and Dpr side chains are removed by treatment with a 20% (v/v) piperidine solution in DMF (15 ml twice for 3 and 7 min.). The condensation between β-amino and β-carboxyl groups is carried out with a 0.25M solution of PyBop in DMF (3 equivalents) in the presence of DIEA (6 equivalents) until negative response of the Kaiser Test.

Activated Boc-Met-OH (0.498 g) in the form of symmetric anhydride is coupled and, after terminal amine group deprotection, the formyl group of tryptophan is deprotected by treatment with 120 ml of 1M solution of TMSiBr and 1M solution of thiosnisole in TFA in the presence of 1.2 ml m-cresol and 1.2 ml EDT. After 1 hour at 0° C., the solution is filtered, the resin washed with TFA and dried. The dry resin is placed in a Teflon reactor with 1 ml anisole and 1 ml dimethyl sulphide. The mixture temperature is brought to −50° C. and 10 ml hydrofluoric acid is distilled therein; then the mixture is kept under stirring for 60 min. in an ice bath. Hydrofluoric aced is removed by nitrogen blowing. The raw product is dried under suction for about 2 hours, is washed with ethyl ether (15 ml twice), extracted in 50% acetic acid (15 ml three times), and filtered in a porous filter funnel to remove the exhaust resin. The resulting solution is diluted with water and freeze-dried. Finally, the peptide is purified by reversed phase chromatography and characterized by analytical HPLC on Varian LC Star 9010 Vydac C18 0.46× 25 cm column with a linear acetonitrile gradient containing 0.1% (v/v) trifluoracetic acid (phase B) vs. 0.1% (v/v) aqueous trifluoracetic acid (phase A), as 5% to 70% phase B, in 50 min., at a rate of 1 ml/min., with 210 nm UV monitoring. Retention time (Rt)=26.3'; chromatographic purity>99%.

FAB-MS: $(M+m)^+=779$.

b) Cyclization of (a)

70 mg product (a) obtained as above is dissolved in 90 ml DMF. The solution is added with 47 mg PyBOP plus 20 µl DIEA. The resulting solution is kept under stirring at 0° C. for 18 hours, then DMF is removed under vacuum and the resulting mixture freeze-dried. Compound (1) is purified by reversed phase liquid chromatography and characterized by analytical HPLC, on Varian LC Star 9010 Vydac C18 0.46×25 cm column with a linear acetonitrile gradient containing 0.1% (v/v) trifluoracetic acid (phase B) vs. 0.1% (v/v) aqueous trifluoracetic acid (phase A), as 5% to 70% phase B, in 50 min., at a rate of 1 ml/min., with 210 nm UV monitoring. Retention time (Rt)=29.5'; chromatographic purity>99%.

FAB-MS: $(M+H)^+=761$.

BIOLOGICAL ACTIVITY

The capacity of the products described in the present invention to interact with the neurokinin A receptor as agonists or antagonists was assessed using a preparation characterized by the fact that the biological response produced by tachykinins and correlated peptides was exclusively determined by the neurokinin A receptor (receptor NK-2). The said preparation consisted of isolated rabbit pulmonary artery affected by a dose-dependent contraction brought about by tachykinins (Rovero et al., Neuropeptides, 13, 263–270, 1989). The determination of the peptide activity in the test preparation was based on the use of an NKA concentration (3 nM) causing a response equal to 45% of max. response. The peptides considered herein were added to the preparation in growing concentrations. Their activity was assessed as inhibition of response to NKA.

By way of example, compound 1 tested at a concentration of 1M caused 100% inhibition of response to neurokinins A in isolated rabbit pulmonary artery.

The capacity of the products described herein to interact with the P substance receptor (receptor NK-1) was assessed through an in vitro test, where the biological response produced by tachykinins and correlated peptides was exclusively determined by the P substance receptor. The test preparation consisted of isolated guinea pig ileum affected by s dose-dependent contraction brought about by tachykinins (Lee et al., Schmied. Arch. Pharmacol., 318, 281–287, 1982). The determination of the activity of the products as per the present invention in the test preparation was based on the use of an SP methyl ester concentration (10 nm) causing s response equal to 45% of max. response (S. Dion et al., Life Sci., 41, 2269–2278, 1987). The products considered herein were added to the preparation in growing concentrations. Their activity was assessed as inhibition of response to SP with satisfactory results.

By way of example, product 1 tested at a concentration of 10 mM caused 100% inhibition of response to SP methyl ester.

Abbreviations used

For the nomenclature and abbreviations of amino acids, reference is made to the rules issued by the IUPAC-IUB Joint Commission on Biochemical Nomenclature (Eur. J. Biochem., 1984, 138:9); unless otherwise specified, amino acids are considered in the L-configuration.

The other abbreviations used are the following:

Boc=tert-butyloxycarbonyl; DCM=dichloromethane; BOP=benzotriazolyl-N-oxytri (dimethylaminophosphonium) hexafluorophosphate, Dpr=2,3-diaminopropionic acid; DCC=N-N'-dicyclohexyl carbodiimide; DCU=N-N' dicyclohexylurea; DIEA= diisopropylethylamine, DMF=N-N' dimethylformamide; EDT=ethandithiol; FAB-MS=fast atoms bombardment mass spectrometry; Fmoc=9-fluorenylmethyloxycarbonyl, HOBt=1-hydroxybenzotriazole; HPLC=high pressure liquid chromatography; iPrOH=isopropanol; PAM= phenylacetsmidomethyl; NKA=neurokinin A; SP=P substance; PIP=piperidine; TFA=trifluoracetic acid; For= formyl; Me=methyl; Ac=acetyl; Fm=fluorenylmethyl; PyBop=benzotriazole-1-yl-oxypyrrolidinephosphonium hexafluorophosphate.

---

We claim:

1. The compounds of formula (I)

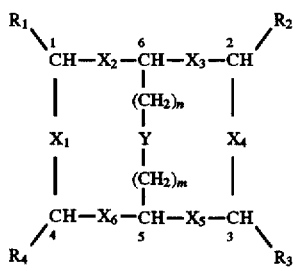

where: the chiral carbons are in the D or L configuration and $X_1$, $X_2$, $X_3$, $X_4$, $X_5$, and $X_6$ are identical or different, and are each selected from the group consisting of —NR'—CO— and —CO—NR'—, where R' is H; Y is selected from the group consisting of —CONR—, —NRCO— and —SS—;

where R is H; wherein: R1 is the same as R2 and is the hydrophobic group consisting of the side chains of amino acids selected from the group consisting of phenylalanine, tyrosine, glycine, alanine, valine, isoleucine, norleucine, norvaline and alloisoleucine; R3 is the hydrophobic group consisting of the side chains of the amino acids selected from tryptophan and phenylalanine, and R4 are the hydrophobic groups consisting of the side chains of amino acids selected from the group consisting of glycine, alanine, valine, leucine, isoleucine, methionine, phenylalanine, tyrosine, norleucine, norvaline, alloisoleucine, cyclohexylglycine (Chg), alpha-amino-n-butyric acid (Aba), cyclohexylalanine (Cha), aminophenylbutyric acid (Pba) and the O-alkylated derivatives of serine, n and m are each independently a whole number from 1 to 4.

2. The compounds of formula (I) according to claim 1 wherein:

R1=—CH$_2$CH(CH$_3$)$_2$

R2=—CH₂C₆H₅

R3 = —CH₂— 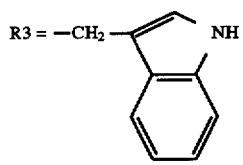

R4=—(CH₂)₂—SCH₃
X1=X2=X3=X4=X5=X6=—CONH—
Y=—CONH—
wherein chiral carbon atoms exhibit the L-configuration.

3. The compounds of formula (I) according to claim 1 wherein:
R1=—CH₂CH(CH₃)₂
R2=—CH₂C₆H₅

R3 = —CH₂— 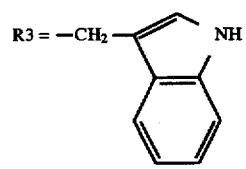

R4=—(CH₂)₂—SCH₃
X1=X2=X3=X4=X5=X6=—CONH—
Y=—NHCO— wherein chiral carbon atoms exhibit the L-configuration.

4. The compounds of formula (I) according to claim 1 wherein:
R1=—CH₂CH(CH₃)₂
R2=—CH₂C₆H₅

R3 = —CH₂— 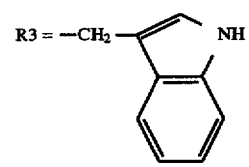

R4=—CH₂—C₆H₁₁
X1=X2=X3=X4=X5=X6=—CONH—
Y=—CONH— wherein chiral carbon atoms exhibit the L-configuration.

5. The compounds of formula (I) according to claim 1 wherein:
R1=—CH₂CH(CH₃)₂
R2=—CH₂C₆H₅

R3 = —CH₂— 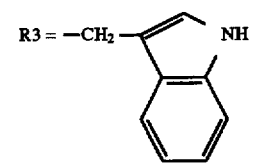

R4=—CH₂—C₆H₁₁
X1=X2=X3=X4=X5=X6=—CONH—
Y=—NHCO— wherein chiral carbon atoms exhibit the L-configuration.

6. The compounds of formula (I) according to claim 1 wherein:

R1=—CH₂CH(CH₃)₂
R2=—CH₂C₆H₅

R3 = —CH₂— 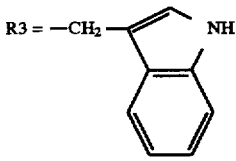

R4=—(CH₂)₂—SCH₃
X1=X2=X3=X4=X5=X6=—CONH—
Y=—SS—
wherein chiral carbon atoms exhibit the L-configuration.

7. The compounds of formula (I) according to claim 1 wherein:
R1=—CH₂CH(CH₃)₂
R2=—CH₂C₆H₅

R3 = —CH₂— 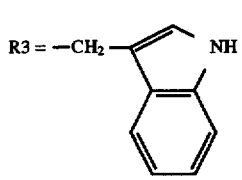

R4=—(CH₂)₂—SCH₃
X1=X2=X3=X4=X5=X6=—CONH—
Y=—CONH—
m=2, n=4 wherein chiral carbon atoms exhibit the L-configuration.

8. The compounds of formula (I) according to claim 1 wherein:
R1=—CH₂CH(CH₃)₂
R2=—CH₂C₆H₅

R3 = —CH₂— 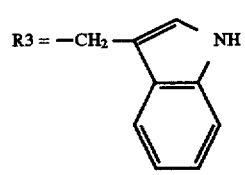

R4=—(CH₂)₂—SCH₃
X1=X2=X3=X4=X5=X6=—NHCO—
Y=—CONH—
m=2, n=4 wherein chiral carbon atoms exhibit the L-configuration.

9. The compounds of formula (I) according to claim 1 wherein:
R1=—CH₂CH(CH₃)₂
R2=—CH₂C₆H₅

R3 = —CH₂— 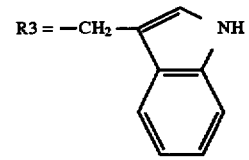

R4=—(CH₂)₂—SCH₃
X1=X2=X3=X4=X5=X6=—NHCO—

Y=—NHCO— m=2, n=4 wherein chiral carbon atoms exhibit the L-configuration.

10. The compounds of formula (I) according to claim 1 wherein:

R1=—CH$_2$CH(CH$_3$)$_2$

R2=—CH$_2$C$_6$H$_5$

R3 = —CH$_2$— 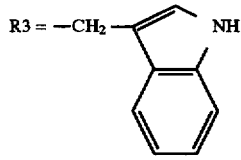

R4=—CH$_2$—C$_6$H$_{11}$

X1=X2=X3=X4=X5=X6=—NHCO—

Y=—CONH— m=2, n=4 wherein chiral carbon atoms exhibit the L-configuration.

11. The compounds of formula (I) according to claim 1 wherein:

R1=—CH$_2$CH(CH$_3$)$_2$

R2=—CH$_2$C$_6$H$_5$

R3 = —CH$_2$— 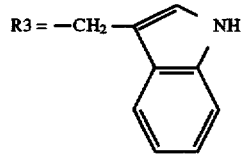

R4=—(CH$_2$)$_2$—SCH$_3$

X1=X2=X3=X4=X5=X6=—NHCO—

Y=—CONH— m=2, n=4 wherein chiral carbon atoms exhibit the L-configuration.

12. The compounds of formula (I) according to claim 1 wherein:

R1=—CH$_2$CH(CH$_3$)$_2$

R2=—CH$_2$C$_6$H$_5$

R3 = —CH$_2$— 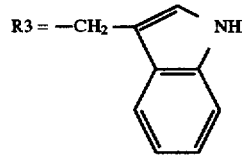

R4=—(CH$_2$)$_2$—SCH$_3$

X1=X2=X3=X4=X5=X6=—NHCO—

Y=—CONH— m=1; n=2 wherein chiral carbon atoms exhibit the L-configuration.

13. The compounds of formula (I) according to claim 1 wherein:

R1=—CH$_2$CH(CH$_3$)$_2$

R2=—CH$_2$C$_6$H$_5$

R3 = —CH$_2$— 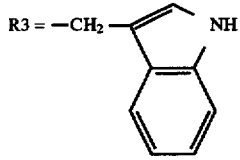

R4=—(CH$_2$)$_2$—SCH$_3$

X1=X2=X3=X4=X5=X6=—NHCO—

Y=—CONH— m=1, n=3 wherein chiral carbon atoms exhibit the L-configuration.

14. The compounds of formula (I) according to claim 1 wherein:

R1=—CH$_2$CH(CH$_3$)$_2$

R2=—CH$_2$C$_6$H$_5$

R3 = —CH$_2$— 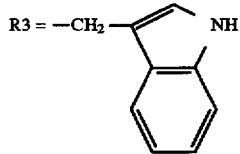

R4=—(CH$_2$)$_2$—SCH$_3$

X1=X2=X3=X4=X5=X6=—NHCO—

Y=—CONH— m=1, n=4 wherein chiral carbon atoms exhibit the L-configuration.

15. The compounds of formula (I) according to claim 1 wherein:

R1=—CH$_2$CH(CH$_3$)$_2$

R2=—CH$_2$C$_6$H$_5$

R3 = —CH$_2$— 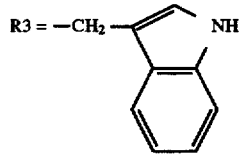

R4=—(CH$_2$)$_2$—SCH$_3$

X1=X2=X3=X4=X5=X6=—NHCO—

Y=—CONH— m=2, n=1 wherein chiral carbon atoms exhibit the L-configuration.

16. The compounds of formula (I) according to claim 1 wherein:

R1=—CH$_2$CH(CH$_3$)$_2$

R2=—CH$_2$C$_6$H$_5$

R3 = —CH$_2$— 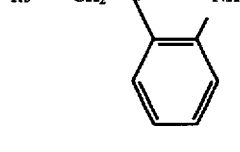

R4=—(CH$_2$)$_2$—SCH$_3$

X1=X2=X3=X4=X5=X6=—NHCO—

Y=—CONH— m=2, n=3 wherein chiral carbon atoms exhibit the L-configuration.

17. The compounds of formula (I) according to claim 1 wherein:

R1=—CH$_2$CH(CH$_3$)$_2$
R2=—CH$_2$C$_6$H$_5$

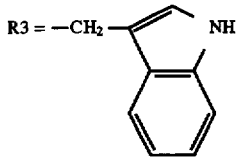

R4=—(CH$_2$)$_2$—SCH$_3$
X1=X2=X3=X4=X5=X6=—NHCO—
Y=—CONH— m=2, n=2 wherein chiral carbon atoms exhibit the L-configuration.

18. The compounds of formula (I) according to claim 1 wherein:

R1=—CH$_2$CH(CH$_3$)$_2$
R2=—CH$_2$C$_6$H$_5$

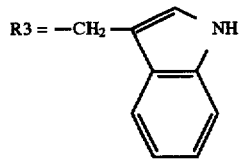

R4=—(CH$_2$)$_2$—SCH$_3$
X1=X2=X3=X4=X5=X6=—NHCO—
Y=—CONH— m=2, n=4 wherein chiral carbon atoms exhibit the L-configuration.

19. The compounds of formula (I) according to claim 1 wherein the carbon atoms in positions 5 and 6 exhibit D-configuration, and

R1=—CH$_2$CH(CH$_3$)$_2$
R2=—CH$_2$C$_6$H$_5$

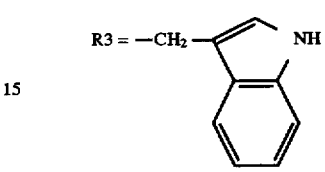

R4=—(CH$_2$)$_2$—SCH$_3$
X1=X2=X3=X4=X5=X6=—NHCO—
Y=—CONH— wherein chiral carbon atoms exhibit the L-configuration.

20. A pharmaceutical composition containing a compound of formula (I) according to claim 1, mixed with suitable carriers.

21. A method for the treatment of hypertension, comprising administering 0.1 to 10 mg active ingredient consisting of the compounds of formula (I) according to claim 1.

* * * * *